(12) United States Patent
Amasia et al.

(10) Patent No.: US 9,186,672 B2
(45) Date of Patent: Nov. 17, 2015

(54) MICROFLUIDIC DEVICE FOR WHOLE BLOOD SAMPLE PREPARATION

(75) Inventors: Mary Amasia, Irvine, CA (US); Marc Madou, Irvine, CA (US)

(73) Assignee: THE REGENTS OF THE UNIVERISTY OF CALIFORNIA, Oakland, CA (US)

( * ) Notice: Subject to any disclaimer, the term of this patent is extended or adjusted under 35 U.S.C. 154(b) by 805 days.

(21) Appl. No.: 13/448,671

(22) Filed: Apr. 17, 2012

(65) Prior Publication Data

US 2012/0295781 A1 Nov. 22, 2012

Related U.S. Application Data

(60) Provisional application No. 61/476,658, filed on Apr. 18, 2011.

(51) Int. Cl.
*B01L 3/00* (2006.01)
*G01N 21/07* (2006.01)
*B01D 21/00* (2006.01)
*B01D 21/26* (2006.01)

(52) U.S. Cl.
CPC ....... *B01L 3/502753* (2013.01); *B01D 21/0003* (2013.01); *B01D 21/262* (2013.01); *G01N 21/07* (2013.01); *B01D 2221/10* (2013.01); *B01L 2200/0621* (2013.01); *B01L 2300/0803* (2013.01); *B01L 2400/0406* (2013.01); *B01L 2400/0409* (2013.01)

(58) Field of Classification Search
CPC ............. B01D 21/0003; B01D 21/262; B01D 2221/10; B01L 3/5027; B01L 3/502753; B01L 2200/0621; B01L 2300/0803; B01L 2300/0806; B01L 2400/0406; B01L 2400/0409; G01N 21/07
See application file for complete search history.

(56) References Cited

U.S. PATENT DOCUMENTS

| | | | |
|---|---|---|---|
| 8,101,138 B2 | 1/2012 | Lee et al. | |
| 8,303,911 B2 | 11/2012 | Siegrist et al. | |
| 2002/0176804 A1* | 11/2002 | Strand et al. | 422/100 |
| 2007/0125942 A1* | 6/2007 | Kido | 250/284 |

(Continued)

OTHER PUBLICATIONS

Cho et al. "One-step pathogen specific DNA extraction from whole blood on a centrifugal microfluidic device" published Feb. 15, 2007, Lab Chip 7, 565-573 (9 pages).

(Continued)

*Primary Examiner* — Timothy Cleveland
(74) *Attorney, Agent, or Firm* — Vista IP Law Group LLP

(57) ABSTRACT

A CD-based device for separating plasma from whole blood includes a substrate, a sedimentation chamber disposed in the substrate, and a collection chamber disposed in the substrate and in fluidic communication with the sedimentation chamber through a siphon channel. The sedimentation chamber includes a plurality of finger-like structures disposed along a radially outward edge of the sedimentation chamber, and protruding radially inward relative to the axis of rotation of the substrate. A method for separating plasma from whole blood using the CD-based device includes introducing a blood sample into the sedimentation chamber, rotating the substrate about an axis of rotation at a first rotational speed to separate the plasma from blood cells, and rotating the substrate about the axis of rotation at a second rotational speed, which is lower than the first rotational speed, to move the plasma from the sedimentation chamber into the collection chamber.

14 Claims, 6 Drawing Sheets

(56) References Cited

U.S. PATENT DOCUMENTS

| | | |
|---|---|---|
| 2008/0110500 A1 | 5/2008 | Kido et al. |
| 2008/0190503 A1 | 8/2008 | Zoval et al. |
| 2011/0094600 A1 | 4/2011 | Bergeron et al. |
| 2012/0028349 A1* | 2/2012 | Giorgini et al. ............... 435/325 |

OTHER PUBLICATIONS

Ducree et al. "The centrifugal microfluidic Bio-Disk platform" published Jun. 28, 2007, Journal of Micromechanics and Microengineering 17 (2007) S103-S115 (13 pages).

Gorkin et al. "Centrifugal microfluidics for biomedical applications" published May 28, 2010, Lab Chip 10, 1758-1773 (16 pages).

Haeberle et al. "Centrifugal extraction of plasma from whole blood on a rotating disk" published Apr. 16, 2006, Lab Chip 6, 776-781 (6 pages).

Kido et al. "A novel, compact disk-like centrifugal microfluidics system for cell lysis and sample homogenization" dated Mar. 27, 2007, Colloids and Surfaces B: Biointerfaces 58 (2007) 44-51 (8 pages).

Kim et al. "Cell lysis on a microfluidic CD (compact disc)" published Aug. 5, 2004, Miniaturisation for Chemistry, Biology & Bioengineering (7 pages).

Lee et al. "A fully automated immunoassay from whole blood on a disc" published Mar. 5, 2009, Lab Chip 9, 1548-1555 (8 pages).

Madou et al. "Lab on a CD" published May 2, 2006, Annu. rev. Biomed. Eng. 2006. 8:601-628 (30 pages).

Martensson et al. "Rapid PCR Amplification of DNA utilizing Coriolis effects." published Mar. 9, 2006, Eur Biophys J (2006) 35: 453-458 (6 pages).

Schembri et al. "Centrifugation and capillarity integrated into a multiple analyte whole blood analyser." Journal of Automatic Chemistry, vol. 17, No. 3 (May-Jun. 1995), pp. 99-104 (6 pages).

"Centrifugal microfluidic platforms for rapid IVDs", http://www.ivdtechnology.com/print/1000 dated Oct. 7, 2010 (9 pages).

* cited by examiner

MICROFLUIDIC DEVICE FOR WHOLE BLOOD SAMPLE PREPARATION

RELATED APPLICATION

This Application claims priority to U.S. Provisional Patent Application No. 61/476,658, filed on Apr. 18, 2011, which is hereby incorporated by reference in its entirety. Priority is claimed pursuant to 35 U.S.C. §119.

STATEMENT REGARDING FEDERALLY SPONSORED RESEARCH OR DEVELOPMENT

This invention was made with government support under grant HR0011-06-1-0050 awarded by the Department of Defense. The government has certain rights in the invention.

FIELD OF THE INVENTION

The present invention pertains to centrifugal microfluidic devices. More specifically, the invention pertains to centrifugal microfluidic devices for the integrated sample preparation of large-volume whole blood samples.

BACKGROUND

Continuous flow systems are an attractive solution for processing large volume blood samples within the framework of microfluidic devices. However, existing continuous flow separation mechanisms are not well suited for handling high hematocrit-level samples. Hematocrit refers the percentage of whole blood that is made up of red blood cells. Non-batch microfluidic devices generally require hematocrit levels ranging from 3% to 25% with the raw blood sample requiring dilution with buffer, and therefore necessitating longer device runs and perhaps additional integrated enrichment or capturing processes.

Centrifugal or compact disc (CD)-based microfluidics offer a simple approach to blood sample preparation as they allow for the multiplexing, automation and miniaturization of the classical blood separation technique based on sedimentation. By exploiting density and size differences between the various blood components, one sediments the denser cellular components of blood and is left with a cell-free plasma sample. The small-volume separation of plasma from both raw and diluted blood samples using centrifugal microfluidic systems has been demonstrated using a CD-based platform. For example, Schembri et al., have demonstrated a multiplexed centrifugal microfluidic device capable of processing a 90 µL whole blood sample by separating and then diluting the plasma into 12 separate testing chambers. See Schembri C. et al., Centrifugation and capillarity integrated into a multiple analyte whole blood analyser. *J. Automat. Chem.* 17, 99-104 (1995). Additionally, Haeberle et al. developed a device to extract 2 µL of plasma from 5 µL of a whole blood sample. Haeberle S. et al., Centrifugal extraction of plasma from whole blood on a rotating disk. *Lab Chip* 6(6), 776-781 (2006). They demonstrated a separation time of about 20 seconds at a moderate spinning frequency of 40 Hz (2400 RPM). The same group also integrated measurement of the concentration of hemoglobin (Hb) or hematocrit levels in human whole blood samples with plasma separation.

SUMMARY

In one embodiment, a centrifugal device for separating plasma from whole blood includes a substrate having an axis of rotation. The substrate may comprise a compact disc. Further, the substrate may comprise multiple layers of polycarbonate.

The centrifugal device further includes a sedimentation chamber disposed in the substrate. The sedimentation chamber has a plurality of finger-like structures disposed along a radially outward edge of the sedimentation chamber. The plurality of finger-like structures protrude radially inward relative to the axis of rotation of the substrate. The centrifugal device may further include a sample inlet in fluidic communication with the sedimentation chamber. The sedimentation chamber may have a volume of at least 2 mL.

The centrifugal device further includes a collection chamber disposed in the substrate and in fluidic communication with the sedimentation chamber. The sedimentation chamber and the collection chamber may be connected by a siphon channel. The centrifugal device may further include a ventilation channel in fluidic communication with the sedimentation chamber and the collection chamber. Still further, the centrifugal device may include a sample outlet in fluidic communication with the collection chamber. The centrifugal device may have a plurality of sedimentation chambers and a plurality of collection chambers disposed in the substrate.

In another embodiment, a method for separating plasma from whole blood includes introducing a blood sample into a sedimentation chamber disposed in a substrate, the sedimentation chamber comprising a plurality of finger-like structures disposed along a radially outward edge of the sedimentation chamber. The blood sample may have a volume of at least 2 mL.

The method further includes rotating the substrate about an axis of rotation at a first rotational speed to separate the plasma from blood cells. The substrate may be rotated at the first rotational speed for at least 2.5 minutes.

The method further includes rotating the substrate about the axis of rotation at a second rotational speed to move the plasma from the sedimentation chamber into a collection chamber disposed in the substrate and fluidically coupled to the sedimentation chamber, wherein the second rotational speed is lower than the first rotational speed, and wherein the plasma in the collection chamber is substantially free of blood cells. The rotational speed of the substrate may be decelerated from the first rotational speed to the second rotational speed at a rate of no more than about 50 RPM/second. The plasma may move from the sedimentation chamber to the collection chamber by flowing through a siphon channel.

Before moving the plasma from the sedimentation chamber into the collection chamber, the method may further include a step of priming the siphon channel by rotating the substrate about the axis of rotation at a third rotational speed, wherein the third rotational speed is less than the first rotational speed and the second rotational speed. For example, the third rotational speed may be no more than 350 RPM. Still further, the method includes removing the plasma from the collection chamber.

In still another embodiment, a system for separating components of a biological sample includes a motor, a rotatable chuck coupled to the motor, and a microfluidic disc configured to be attached to the chuck. The microfluidic disc comprises an axis of rotation, a sedimentation chamber comprising finger-like structures protruding radially inward relative to the axis of rotation, a collection chamber, and a siphon channel in fluidic communication with the sedimentation chamber and the collection chamber. The sedimentation chamber may have a volume of at least 2 mL.

The system further includes a control system coupled to the motor, wherein the control system is configured to rotate the disc about the axis of rotation at a first rotational speed until the sample components are separated within the sedimentation chamber. The control system may be configured to rotate the disc at the first rotational speed for at least 2.5 minutes. The control system is further configured to rotate the disc about the axis of rotation at a second rotational speed in order to prime the siphon channel. The second rotational speed may be not more than 350 RPM. The control system is further configured to rotate the disc about the axis of rotation at a third rotational speed in order to move one of the sample components into the collection chamber while another sample component remains in the sedimentation chamber. The biological sample may be a blood sample, wherein the one of the sample components may be plasma, and another sample component may be blood cells.

BRIEF DESCRIPTION OF THE DRAWINGS

FIG. 4A is a photographic image taken at time=0 seconds. FIG. 4B is a photographic image taken at time=20 seconds. FIG. 4C is a photographic image taken at time=150 seconds. FIG. 4D is a photographic image taken at time=240 seconds. FIG. 4E is a photographic image taken at time=280 seconds. FIG. 4F is a photographic image taken at time=310 seconds.

DETAILED DESCRIPTION OF THE ILLUSTRATED EMBODIMENTS

The description that follows relates to a large-volume centrifugal or CD-based device for blood plasma separation from blood cells (e.g., red blood cells, etc.). However, it is to be understood that, while the invention lends itself well to blood plasma separation, the invention, in its broadest aspects, may not be so limited. For example, the separation device described below may be used for separating other samples having two or more components, such as saliva, urine, milk, and the like.

The CD-based device described herein integrates microfluidic device principles with real-world large sample volume. For example, the CD-based device described herein may be capable of processing 2 mL undiluted blood samples to yield high purity plasma in less than half the time of commercial plasma preparation tubes. This large volume CD-based device automates the plasma collection into a separate chamber, removing the additional step of manual pipetting. The CD-based device may alternatively be referred to herein as a disc, CD device, substrate, microfluidic disc, centrifugal device, or other similar nomenclature.

Figure 1:
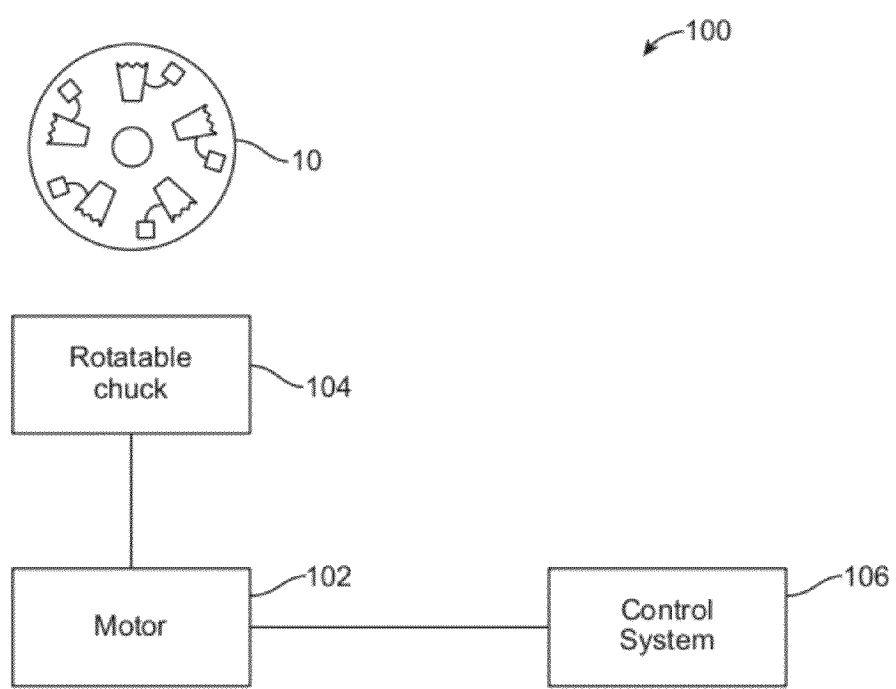
FIG. 1 is a block diagram of a system for separating components of a biological sample according to one embodiment.

The CD-based device is part of a system 100, shown in FIG. 1, for separating components of a biological sample. The system 100 includes a motor 102, and a rotatable chuck 104 coupled to the motor 102. The CD-based device 10 is configured to be attached to the chuck 104 such that rotational motion from the motor 102 can be imparted to the CD-based device 10. The chuck 104 may pinch the CD-based device 10 or may rely on gravitational or frictional support (e.g., spindle) to hold the same. Various chuck 104 configurations such as those used to spin CDs, DVDs, and the like may be employed. The system 100 also includes a control system 106 coupled to the motor 102. The control system 106 and motor 102 are used to control the spin speed, acceleration and deceleration rates, and absolute position of the CD-based device 10. The control system 106 may include a computer or the like having one or more processors (not shown) contained therein for carrying out a pre-programmed set of instructions (e.g., software) for the spin speed, acceleration, deceleration, and absolute position of the CD-based device 10. Alternatively, the control system 106 may include one or more dedicated processors that contain or are configured to contain instructions therein. Regardless, the control system 106 interfaces with the motor 102 such that the motor 102 is controlled by the control system 106.

Figure 2:
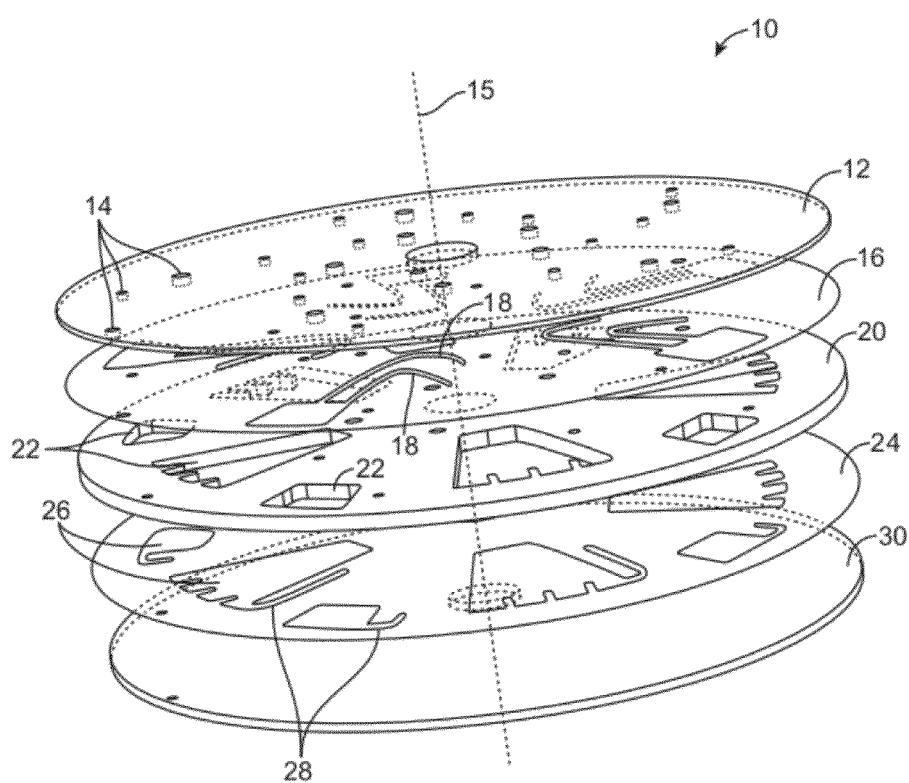
FIG. 2 is an exploded view of the layers of the CD-based device used in the system of FIG. 1.

As shown in FIG. 2, the CD-based device 10 may be a multi-layer device comprising (3) three layers of plastic discs held together by layers of adhesive. Of course, more or less layers may be employed in other embodiments. Referring to FIG. 2, the top disc 12 comprises inlet and vent holes 14, and may be about 1/16 inches thick. The top adhesive layer 16 comprises channels 18, and may be about 0.004 inches thick. The middle disc 20 comprises chambers 22, and may be about 1/8 inches thick. The bottom adhesive layer 24 comprises chambers 26 and channels 28, and may be about 0.004 inches thick. The bottom disc 30 may be about 1/16 inches thick. It should be noted that the dimensions recited herein are exemplary only, and that the layers 12, 16, 20, 24, 30 of the CD device 10 may have thicknesses greater or less than those recited above. The plastic surfaces may be subjected to oxygen plasma treatment to ensure that all surfaces in contact with liquids are rendered hydrophilic. Each of the layers 12, 16, 20, 24, 30 of the CD device 10 has a central opening surrounding the axis of rotation 15 of the CD device 10.

The plastic disc layers 12, 20, and 30 may be formed of polymer material such as polycarbonate. For example, the plastic disc layers 12, 20, and 30 may be cut from stock polycarbonate sheets using a computer-numerical control machine. The adhesive layers 16 and 24 may be double-sided pressure-sensitive adhesives (PSA). A cutter-plotter may be used to cut the PSA layers. After the five layers 12, 16, 20, 24, and 30 are machined, they may be aligned and pressed together with a manual press. Thus, the layers of polycarbonate 12, 20, and 30 are permanently bonded together with the PSA layers 24 and 30 to form a monolithic device 10. Alternatively, the CD device 10 may be formed by injection molding or hot embossing.

The CD device 10 shown in FIGS. 1 and 2 is depicted as having five separation devices equally spaced about the axis of rotation 15 of the disc 10. However, it should be well understood that more or fewer separation devices may be formed on a single CD.

Figure 3:
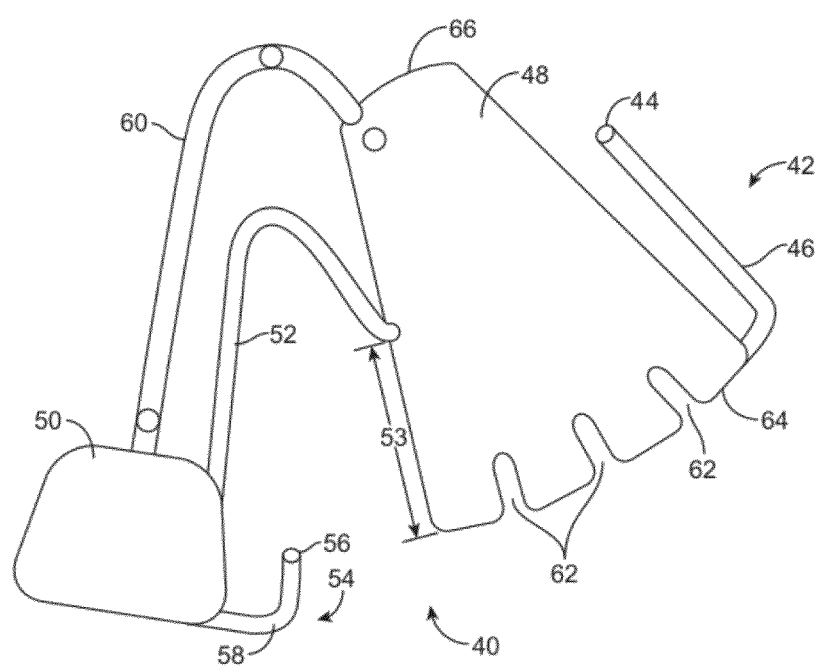
FIG. 3 is a detailed view of one of the separation devices formed on the CD-based device shown in FIG. 2.

A single separation device 40 formed on the CD device 10 is depicted in FIG. 3. The separation device 40 includes a sample inlet 42 comprising an inlet hole 44 and an inlet channel 46. A sedimentation chamber 48 is in fluidic communication with the inlet hole 44 through the inlet channel 46. The sedimentation chamber 48 has a radially outward edge 64 adjacent to the outside edge of the disc 10, and a radially inward edge 66 adjacent to or near the axis of rotation 15, or center, of the disc 10. The volume of the sedimentation chamber 48 is greater than 2 mL. Due to the relatively large volume of the samples processed using the disc 10 (e.g., 2 mL versus 90 µL in small sample volume CD-based devices), relatively high pressure may be exerted on the outer edge 64 of the sedimentation chamber 48 during centrifugation. To counteract any negative effects from the heightened pressure, the top and bottom polycarbonate layers 12, 30 of the disc 10 may be relatively thick so that the sedimentation chamber 48 is less susceptible to deformation and subsequent delamination of the layers of the disc 10 which can cause leakage of fluid and material from between the layers of the disc. For example, as discussed above, the top and bottom polycarbonate layers, 12 and 30, may be about 1/16 inches thick. However, it should be well understood that other thicknesses are within the scope of the embodiments discussed herein.

Still referring to FIG. 3, finger-like structures 62 are disposed along the radially outward edge 64 of the sedimentation chamber 48 and help to counteract any negative effects from the heightened pressure. The finger-like structures 62 protrude radially inward relative to the axis of rotation 15 of the disc 10. The finger-like structures 62, which may be, for example, approximately 0.255 inches by 0.074 inches (other dimensions may also be used), increase the surface area between the plastic layers 12, 20, 30 of the disc 10, allowing for more adhesive contact and, therefore, a stronger bond. The finger-like structures 62 may help to lessen the pressure along the outer radius 64 of the sedimentation chamber 48 by distributing the centrifugal force over a larger surface area. Along with the thicker top and bottom plastic layers 12, 30, the finger-like structures 62 may reduce or eliminate delamination which results in fluid leakage during processing of the large-volume samples. Although (3) three finger-like structures 62 are depicted in FIG. 3, it should be understood that the sedimentation chamber 48 may include more than three or less than three finger-like structures.

The separation device 40 shown in FIG. 3 also includes a collection chamber 50 in fluidic communication with the sedimentation chamber 48 by way of a siphon channel 52. The collection chamber 50 is located radially outward relative to the sedimentation chamber 48. The diameter of the siphon channel 52 is such that the siphon channel 52 exerts a capillary force on the sample within the sedimentation chamber 48. When the disc 10 spins at a high speed, the centrifugal force resists the capillary action of the siphon channel 52, and the meniscus front does not go past the siphon crest. Only when the spin speed is reduced to a low rotations per minute (RPM) does the capillary force overwhelm the centrifugal force, and surface tension pulls the meniscus over the crest, or "primes" the siphon channel 52. After the siphon channel 52 is primed, the rotational speed may be increased again for fluid transfer from the sedimentation chamber 48 into the collection chamber 50.

The height 53 of the siphon channel 52 is the distance between the outward edge 64 of the sedimentation chamber 48 and the inlet of the siphon channel 52. In order to obtain a substantially pure plasma sample, the height 53 of the siphon channel 52 should be above the height of the plasma-blood cell interface that is created when the blood components separate during centrifugation. The height of the plasma-blood cell interface is dependent upon the hematocrit level of the whole blood sample. Hematocrit levels in blood vary depending on the gender, health, and species of the donor, with human blood ranging from 30 to 52% hematocrit. To account for these expected variations in the amount of red blood cells, the height 53 of the siphon channel 52 may be at a level above the volume of blood cells according to a 52% hematocrit level. For example, the height 53 of the siphon channel 52 may be around 1 inch or less (e.g., 0.8 inches or less). In this manner, only the cell-free plasma portion of the sample may be transferred through the siphon channel 52 to the collection chamber 50.

The separation device 40 shown in FIG. 3 further includes a sample outlet 54 comprising a collection hole 56 and a collection channel 58. The collection hole 56 is in fluidic communication with the collection chamber 50 by way of the collection channel 58.

A ventilation channel 60 in fluidic communication with the sedimentation chamber 48 and the collection chamber 50 allows for "self-venting." As fluid fills up the collection chamber 50 or the sedimentation chamber 48, displaced air is able to move back towards the disc center via the ventilation channel 60. Thus, fluid samples within the separation device 40 may be fully sealed off from the environment, thereby minimizing exposure to device users and possible contamination from the environment.

Figure 4A:
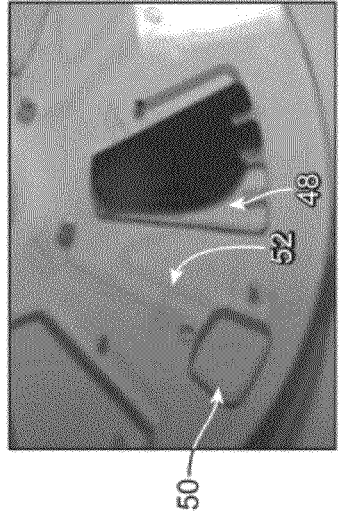
FIGS. 4A-4F are photographic images depicting various steps in a method for separating plasma from whole blood using the CD-based device shown in FIGS. 1-3.
Figure 4B:
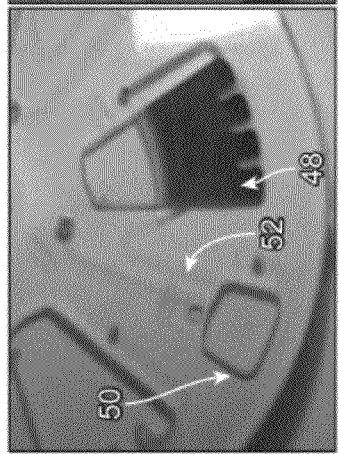
Figure 4C:
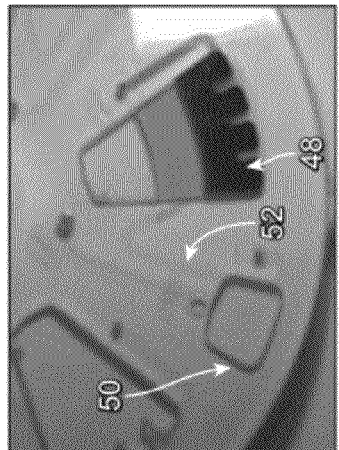

A method for separating plasma using the CD device 10 will now be described with reference to FIGS. 4A-4F. First, as shown in FIG. 4A, a blood sample is introduced into the sedimentation chamber 48. The volume of the blood sample may be about 2 mL, and the volume of the sedimentation chamber 48 may be greater than 2 mL. After the sample is introduced, all vent and inlet holes may be sealed off from the environment using, for example, an adhesive-backed thin film. The disc 10 may then be rotated at an acceleration rate of about 500 RPM/s up to a sedimentation speed of about 3800 RPM. The disc 10 may remain at the sedimentation speed until the plasma is sufficiently separated from the blood cells. Using the disc 10, sufficient plasma separation occurs in about 2.5 to 20 minutes. Cell sedimentation is shown in FIGS. 4B and 4C.

Figure 4D:
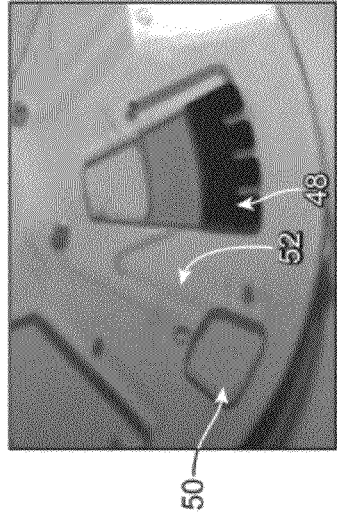

After sedimentation, the disc 10 may be decelerated at a rate of about 50 RPM/s down to a rotational speed of about 350 RPM in order to prime the siphon channel 52. This relatively slow deceleration may minimize perturbations to the plasma-blood cell interface. If the deceleration occurs too quickly, sedimented cells may mix with the separated plasma, negatively impacting the purity of the plasma sample. Similarly, if the siphon priming speed is too low, the interface between blood cells and plasma may be compromised and purity will drop. The siphon-priming step is depicted in FIG. 4D.

Figure 4E:
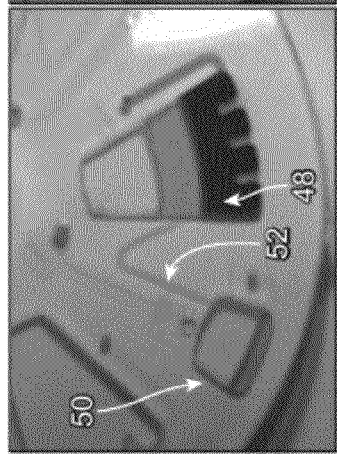
Figure 4F:
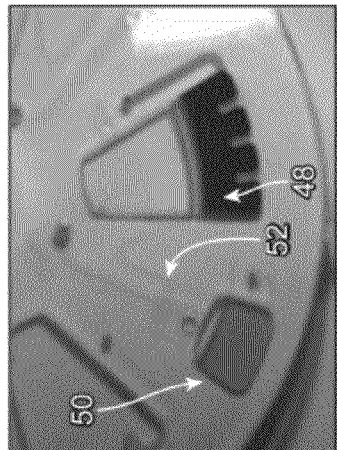
Figure 5:
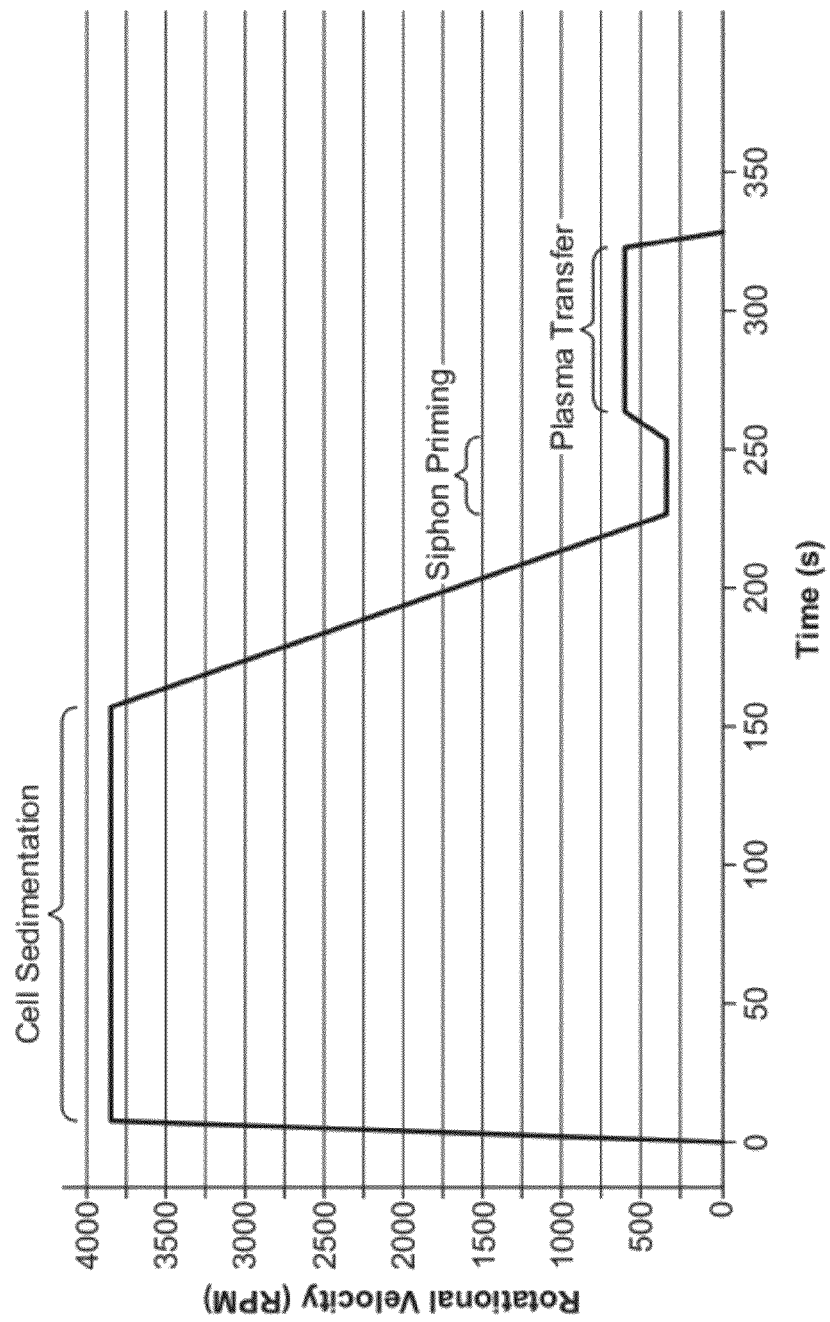
FIG. 5 illustrates the spin profile graph detailing the rotational velocity of the CD device 10 as a function of time as discussed above. The processes of cell sedimentation, siphon priming, and plasma transfer are illustrated.

After about 30 seconds at the siphon priming speed (e.g., about 350 RPM), the siphon channel 52 may be fully primed. Next, the spin speed may be increased at a rate of about 20 RPM/s to a rotational speed of about 600 RPM to transfer the separated plasma sample into the lower collection chamber 50 while the blood cells remain in the sedimentation chamber 48. FIG. 4E depicts the collection chamber 50 beginning to fill, and FIG. 4F depicts the collection chamber 50 being almost completely full of substantially pure plasma. FIG. 5 illustrates the spin profile graph detailing the rotational velocity of the CD device 10 as a function of time as discussed above. The processes of cell sedimentation, siphon priming, and plasma transfer are illustrated.

After centrifugation, the plasma samples are collected from the disc 10 by removing all sealant films, and removing the plasma sample from the collection chamber 50 via the plasma collection hole 56 using, for example, a pipette, a syringe, or the like. The rotation speeds, acceleration rates, and deceleration rates recited above are exemplary only. It should be well understood that rotation speeds, acceleration rates, rotational times (e.g., duration of rotation at a particular RPM), and deceleration rates greater than or less than those recited above are within the scope of the embodiments described herein.

Figure 6:
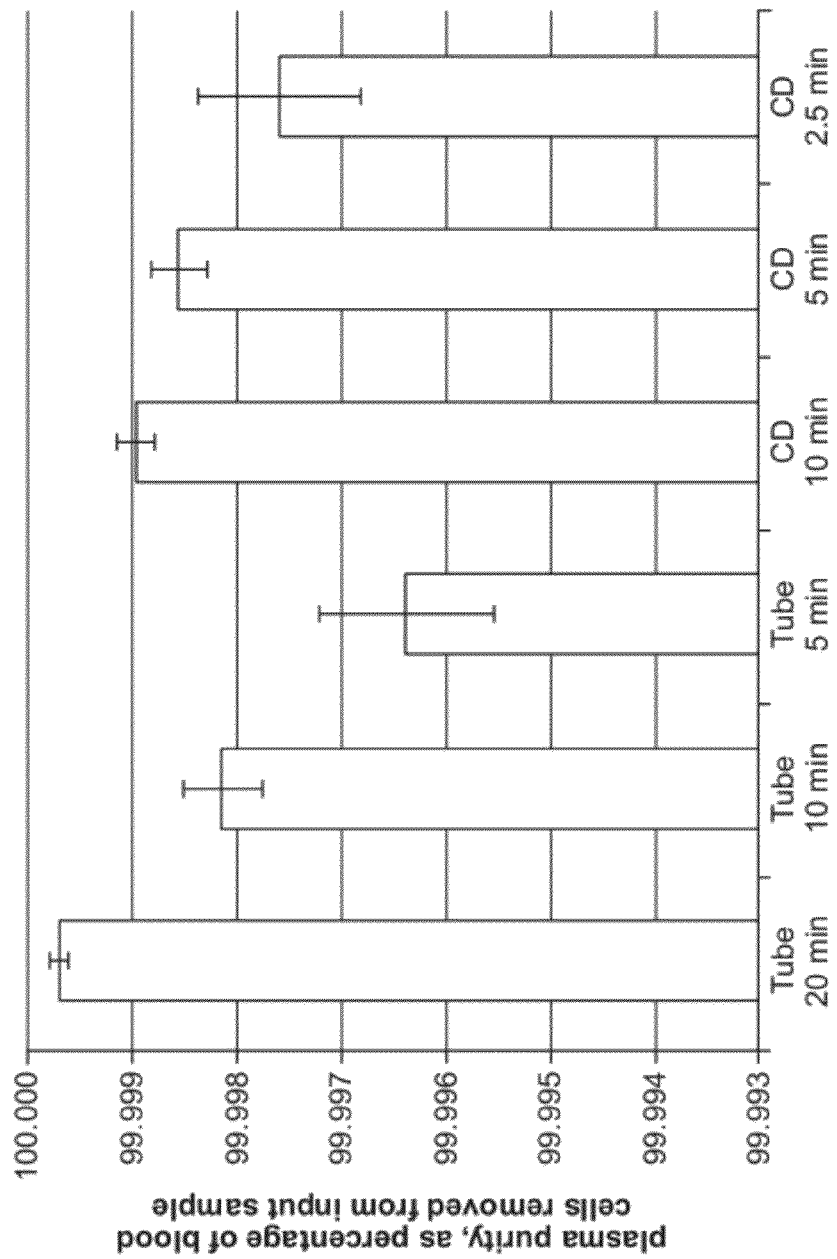
FIG. 6 illustrates a purity comparison graph between commercial plasma preparation tubes and the large volume CD device 10. For the same duration of sedimentation time, the CD device 10 yielded plasma of equal or greater purity than the tube format. Error bars represent one standard deviation from three samples (n=3).

Processing blood samples using the CD device 10 resulted in very high purity plasma samples. For example, the purity, or the percentage of blood cells removed from the starting raw blood sample was much greater than 99%. Compared to the plasma purity obtained using commercially available plasma preparation tubes and table-top centrifuges, the plasma purity obtained with the CD device 10 described herein was higher for the sample sedimentation time. Notably, a sedimentation time of 2.5 minutes resulted in plasma purity levels of about 58% for tube devices, and 99.997% using the CD device 10. FIG. 6 illustrates a purity comparison graph between commercial plasma preparation tubes and the large volume CD device 10. For the same duration of sedimentation time, the CD device 10 yielded plasma of equal or greater purity than the tube format. Error bars represent one standard deviation from three samples (n=3).

The total process time, including acceleration and deceleration times for the CD-based device 10, is 320 seconds, much faster than a floor centrifuge, which requires a long deceleration phase so that the separated plasma is not disturbed from rapid deceleration of the rotor. This CD-based device 10 automates the plasma collection into a separate chamber, removing the additional step of manual pipetting, thereby removing the need for this slow deceleration final step since the plasma is already separated into another chamber and is no longer at risk of cell resuspension.

While embodiments have been shown and described, various modifications may be made without departing from the scope of the inventive concepts disclosed herein. The invention(s), therefore, should not be limited, except to the following claims, and their equivalents.

What is claimed is:

1. A centrifugal device for separating plasma from whole blood, comprising:
   a multilayer substrate having an axis of rotation;
   a sedimentation chamber disposed in one of the layers of the multilayer substrate and defining an interior volume having a volume of at least 2 mL, the sedimentation chamber comprising a plurality of finger-like structures disposed along a radially outward edge of the sedimentation chamber, the plurality of finger-like structures protruding radially inward relative to the axis of rotation of the multilayer substrate and into the interior volume; and
   a collection chamber disposed in the multilayer substrate and in fluidic communication with the sedimentation chamber.

2. The centrifugal device of claim 1, wherein the sedimentation chamber and the collection chamber are connected by a siphon channel.

3. The centrifugal device of claim 1, further comprising a sample inlet in fluidic communication with the sedimentation chamber.

4. The centrifugal device of claim 1, further comprising a ventilation channel in fluidic communication with the sedimentation chamber and the collection chamber.

5. The centrifugal device of claim 1, further comprising a sample outlet in fluidic communication with the collection chamber.

6. The centrifugal device of claim 1, further comprising a plurality of sedimentation chambers and a plurality of collection chambers disposed in the multilayer substrate.

7. The centrifugal device of claim 1, wherein the multilayer substrate comprises a compact disc.

8. The centrifugal device of claim 1, wherein the multilayer substrate comprises multiple layers of polycarbonate.

9. A centrifugal device for separating plasma from whole blood comprising:
   a multilayer substrate having an axis of rotation;
   an inlet channel disposed in the substrate multilayer and including an inlet hole;
   a sedimentation chamber disposed in one of the layer of the multilayer substrate and coupled to the inlet channel, the sedimentation chamber defining an interior volume having a volume of at least 2 mL and comprising a plurality of finger-like structures disposed along a radially outward edge of the sedimentation chamber, the plurality of finger-like structures protruding radially inward relative to the axis of rotation of the multilayer substrate and into the interior volume;
   a collection chamber disposed in the multilayer substrate and at least part of which is radially outward of the sedimentation chamber, the collection chamber in fluidic communication with the sedimentation chamber via a siphon channel; and
   a ventilation channel disposed in the multilayer substrate and connecting the sedimentation chamber and the collection chamber.

10. The device of claim 9, further comprising a collection channel connected to the collection chamber and terminating in a collection hole.

11. The device of claim 10, further comprising a removable seal disposed above the inlet hole and the collection hole.

12. The centrifugal device of claim 9, wherein the multilayer substrate comprises multiple layers of polycarbonate.

13. The centrifugal device of claim 1, wherein each of the finger-like structures has a length of about 0.26 inches and a width of about 0.07 inches.

14. The centrifugal device of claim 1, wherein the multilayer substrate comprises top and bottom polycarbonate layers having a thickness of about 0.0625 inches.

* * * * *